United States Patent [19]

Oh et al.

[11] Patent Number: 5,384,424
[45] Date of Patent: Jan. 24, 1995

[54] PROCESS FOR THE SELECTIVE PREPARATION OF 4,4-METHYLENE-BIS-(N-PHENYLALKYL-CARBAMATE)

[75] Inventors: Jae S. Oh; Eung J. Kim, both of Daejeon, Rep. of Korea

[73] Assignee: Lucky Limited, Seoul, Rep. of Korea

[21] Appl. No.: 904,736

[22] Filed: Jun. 25, 1992

[30] Foreign Application Priority Data

Jun. 26, 1991 [KR] Rep. of Korea ............. 91-10676
Dec. 24, 1991 [KR] Rep. of Korea ............. 91-24291

[51] Int. Cl.$^6$ .......................................... C07C 261/00
[52] U.S. Cl. .............................................. 560/25
[58] Field of Search ................................... 560/25

[56] References Cited

U.S. PATENT DOCUMENTS

| | | | |
|---|---|---|---|
| 2,946,768 | 7/1960 | Klauke | 560/25 |
| 4,162,362 | 7/1979 | Shawl | 560/25 |
| 4,287,132 | 9/1981 | Mameniskis | 260/453 P |

FOREIGN PATENT DOCUMENTS

| | | |
|---|---|---|
| 0216273 | 1/1987 | European Pat. Off. . |
| 55-129260 | 10/1980 | Japan . |
| 57-171953 | 10/1982 | Japan . |
| 58-62151 | 4/1983 | Japan . |
| 59-172451 | 9/1984 | Japan . |
| 60-231640 | 11/1985 | Japan . |
| 60-237058 | 11/1985 | Japan . |
| 1398975 | 6/1975 | United Kingdom . |
| 1520055 | 8/1978 | United Kingdom . |

*Primary Examiner*—Paul Killos
*Attorney, Agent, or Firm*—Anderson Kill Olick & Oshinsky

[57] ABSTRACT

The present invention relates to a process for the selective preparation of 4,4-methylene-bis-(N-phenylalkylcarbamate) which comprises condensing N-phenylalkylcarbamate with a methylating agent in the presence of an acidic ion-exchange resin or an aqueous acid as a catalyst and a non polar aprotic solvent and filtrating a condensation product at a temperature greater than the melting point of N-phenylalkylcarbamate to separate 4,4-methylene-bis-(N-phenylalkylcarbamate).

16 Claims, No Drawings

PROCESS FOR THE SELECTIVE PREPARATION OF 4,4-METHYLENE-BIS-(N-PHENYLALKYLCARBAMATE)

FIELD OF THE INVENTION

The present invention relates to a process for the selective preparation of 4,4-methylene-bis-(N-phenylalkylcarbamate); and, more specifically, to a process which comprises: condensing N-phenylalkylcarbamate with a methylating agent in the presence of an acidic ion-exchange resin or an aqueous inorganic acid as a catalyst, and a non-polar aprotic solvent; and filtrating the obtained crystalline product in an emulsion at a temperature greater than the melting point of N-phenylalkylcarbamate to selectively separate 4,4-methylene-bis-(N-phenylalkylcarbamate).

BACKGROUND OF THE INVENTION 4,4-methylene-bis-(N-phenylalkylcarbamate) is a precursor to 4,4-diphenylmethanediisocyanate (hereinafter referred to as pure MDI) which is useful for the preparation of a polyurethane and in various other expanding fields of application. For instance, pure MDI is used for the preparation of polyurethane elastomer or spandex, or in the coating process of artificial leather; and crude MDI which can be formed from 2,4-methylene-bis-(N-phenylalkylcarbamate) and trimer or tetramet thereof, etc., is used as an insulator for such products as refrigerator, air conditioner, etc., an engineering plastic material for such automobile components as steering wheel and bumper or as a synthetic wood material.

Conventionally, 4,4-methylene-bis-(N-phenylalkylcarbamate) is prepared by reacting N-phenylalkylcarbamate with a methylating agent such as formalin in the presence of an acid catalyst and a suitable solvent, as shown in the following scheme 1:

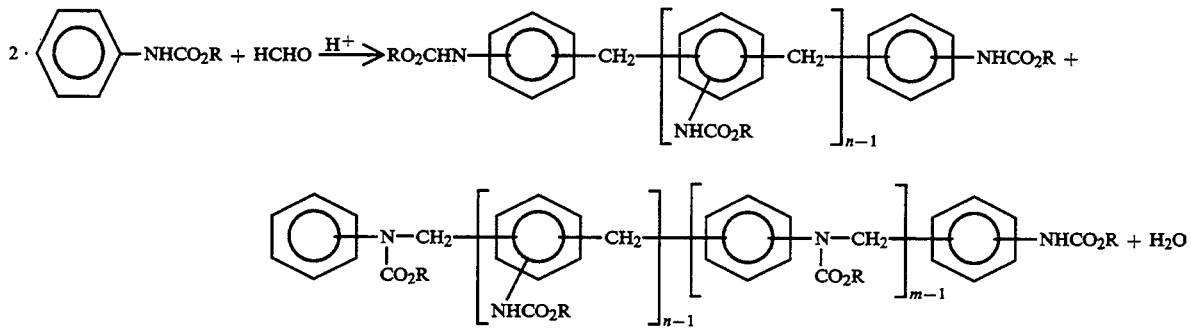

Scheme 1 wherein:

R is a lower alkyl group having 8 or fewer carbon atoms, and n and m are independently an integer of 1 to 5.

However, the above process yields a large amount of isomeric products, e.g., 2,4-methylene-bis-(N-phenylalkylcarbamate) and trimer or tetramer thereof, etc., (or polymethylene polyphenylalkylcarbamate) and undesired N-benzyl compounds, e.g., N-(alkoxycarbonyl, phenylaminomethylphenyl and trimer or tetramer thereof, etc., in addition to the desired product of 4,4-methylene-bis-(N-phenylalkylcarbamate); and, consequently, an additional procedure for isolating the by-products is required. When the reaction is carried out in water as a solvent, it produces a large amount of undesired N-benzyl compounds due primarily to a reaction occurring relative to a nitrogen atom of N-phenylalkylcarbamate.

It has further been proven very difficult to selectively separate 4,4-methylene-bis-(N-phenylalkylcarbamate) alone from the products produced by condensation of N-phenylalkylcarbamate with a methylating agent by using a conventional process such as distillation since some of the products, e.g., 4,4-methylene-bis-(N-phenylalkylcarbamate), 2,4-methylene-bis-(N-phenylalkylcarbamate), polymethylene polyphenylalkylcarbamate and N-benzyl compounds, have similar physical properties and high boiling points and, moreover, are unstable at a high temperature.

For instance, Japanese Laid-open Patent Application No. Sho 59-172451 discloses a process which comprises condensing N-phenylalkylcarbamate with a methylating agent such as formalin, trioxane or paraformaldehyde in the presence of an inorganic liquid acid, e.g., hydrochloric, sulfuric or phosphoric acid as a catalyst and water as a solvent. However, it has the disadvantage that large amounts of by-products, e.g., N-benzyl compounds, are produced; and, as a result, the desired compound cannot be obtained in a sufficient selectivity. Further, it is difficult to separate and recover the desired compound in a commercial scale because the product is combined with the by-products to form large solid chunks.

Japanese Laid-open Patent Application Nos. Sho 55-129260, 57-171953 and 58-62151 and U.S. Pat. No. 4,162,362 are directed to various condensation processes conducted in the presence of various Brønsted acids comprising trifluoromethanesulfonic acid, sulfonic fluoride, carboxylic acid, etc., or various Lewis acids comprising iron chloride on graphite, boron trifluoride, etc., as a catalyst; and nitrobenzene, benzene and sulfolane as an organic solvent. However, these processes suffer from the common deficiency of producing a low yield of 30 to 50% of 4,4-methylene-bis-(N-phenylalkylcarbamate) owing to, e.g., the high acidity of the catalyst used and a large amount of polymethylene polyphenylalkylcarbamate, which aggravates the task of selectively preparating 4,4-methylene-bis-(N-phenylalkylcarbamate).

The processes disclosed in Japanese Laid-open Patent Application Nos. Sho 60-237058 and 60-231640 employ a mixture of methylene-(N-phenylalkylcarbamate) and polymethylene polyphenylalkylcarbamate pyrolyzed at a high temperature in the presence of a suitable solvent and a catalyst to obtain a mixture of 4,4-diphenylmethanediisocyanate and polymethylene polyphenylisocyanate; and the isocyanate mixture is evaporated in a thin film evaporator at a high temperature under a vaccum for the prevention of polymerization of the products to separate a portion of 4,4-diphenylmethanediisocyanate as described in British Patent Nos. 1398975 and 1520055. These processes have the similar defect of a low selectivity for 4,4-diphenylmethane diisocyanate and require expensive equipments, complicated techniques and a high consumption of energy to meet the requirements of maintaining high temperatures and vaccum condition.

As a result, needs have continued to exist for the development of a process for the preparation of 4,4-methylene-bis-(N-phenylalkylcarbamate) in a high selectivity, with a reduced level of by-products and at a lower cost.

SUMMARY OF THE INVENTION

The present inventors have now developed a novel process for selectively preparing 4,4-methylene-bis-(N-phenylalkylcarbamate) alone which is a precursor to pure MDI by way of: using an acidic ion-exchange resin or an aqueous inorganic acid as a catalyst, and a non-polar aprotic solvent; and filtrating the crystalline reaction product at a temperature greater than the melting point of N-phenylalkylcarbamate to separate 4,4-methylene-bis-(N-phenylalkylcarbamate).

Specifically, the process of the present invention generates a low level of by-products, which produces 4,4-methylene-bis-(N-phenylalkylcarbamate) in a high yield and selectivity.

DETAILED DESCRIPTION OF THE INVENTION

The novel process of the present invention, capable of highly selectively preparing 4,4-methylene-bis-(N-phenylalkylcarbamate) of formula (I), comprises: condensing N-phenylalkylcarbamate represented by formula (II) with a methylating agent in the presence of an acidic ion-exchange resin or an aqueous inorganic acid and a non-polar aprotic solvent to obtain a crystalline compound of formula (III) in an emulsion; and filtrating the compound of formula (III) at a temperature greater than the melting point of N-phenylalkylcarbamate to separate 4,4-methylene-bis-(N-phenylalkylcarbamate):

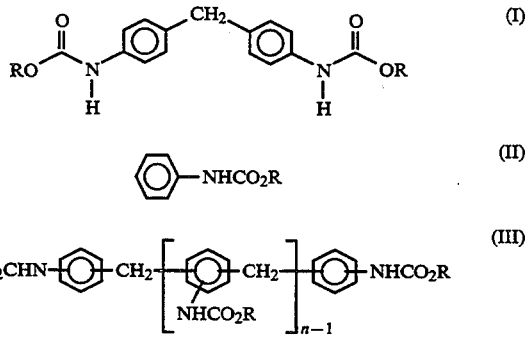

wherein:

R is a lower alkyl group having 8 or fewer carbon atoms, and n is an integer of 1 to 5.

The preferred compounds of formula (II) for the present invention include: methyl N-phenylcarbamate, ethyl N-phenylcarbamate, n-propyl N-phenylcarbamate, isopropyl N-phenylcarbamate, n-butyl N-phenylcarbamate, isobutyl N-phenylcarbamate, t-butyl N-phenylcarbamate, pentyl N-phenylcarbamate and the isomers thereof, hexyl: N-phenylcarbamate and the isomers thereof; cyclohexyl N-phenylcarbamate, heptyl N-phenylcarbamate and the isomers thereof; and octyl N-phenylcarbamate and the isomers thereof. Among these compounds, methyl N-phenylcarbamate, ethyl N-phenylcarbamate and propyl N-phenylcarbamate are particularly preferred.

The methylating agents suitable for use in the present invention are formalin, paraformaldehyde, trioxane, dialkoxymethane, 1,3-dioxane and hexamethylenetetramine, preferably formalin, paraformaldehyde, trioxane and dialkoxymethane wherein alkoxy groups have preferably $C_1$ to $C_6$ such as dimethoxymethane, diethoxymethane, dipropoxymethane, dipentoxymethane or dihexoxymethane. The methylating agents may be used alone or in a mixture thereof.

The acidic ion-exchange resin suitable for use in the present invention is a styrene-based sulfonic acid resin, which can be represented by formula (IV) having sulfonic groups of at least 3 milliequivalents (meq/g) as a functional group, and surface area per weight of at least 50 m²/g:

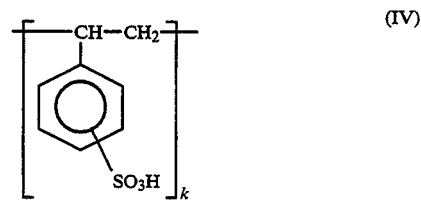

wherein:

k is preferably $10^2$ to $10^4$.

The swelling property of the resin depends on the value of k, i.e., the molecular weight. The sulfonic group may be introduced to any of the ortho, meta and para positions in the phenyl ring of the styrene resin, preferably to the para position. The styrene resin used in the present invention is preferably in the form of spherical granules having a diameter of 0.1 to 1.0 mm to facilitate the reaction and the separation and recovery of the catalyst. The catalyst resin should have a network structure having a crosslinking density to the extent that it makes easy adsorption and desorption of the reactants and the products. It is preferred for the styrene resin to be crosslinked so as to contain 10 to 25% by weight of a crosslinking agent, divinylbenzene. In general, if the crosslinking density is higher, the mechanical properties of a solid acid resin are improved but it is difficult for the reactants to penetrate into the inner pores of the resin; conversely, if it is lower, the reaction proceeds over the entire surface of the catalyst, but the life time of the catalyst tends to be shortened because of the easiness of aging; and, further, it is difficult to separate the reaction product from the solvent. The arrangement of sulfonic groups in the crosslinked ion exchange resin of formula (IV) is also crucial since the reaction should proceed not only on the surface but also in the inner pores of the catalyst. The properties of the catalyst depend somewhat on the ratio of the sulfonic groups in the surface to those in the inner pores of the catalyst. It is required in the present invention that 5% or more of the total sulfonic groups be present in the inner pores of the catalyst.

The important feature of the solid acid resin resides in that a lower amount of the solid acid resin brings an almost equivalent yield to that of a liquid acid during the same reaction period, which enables one to overcome the problems associated with using a liquid acid in carrying the reaction. The amount of a solid acid resin used is crucial and correlative with the number of sulfonic groups present in the resin and the percentage that they are present on the surface and in the inner pores of the catalyst, respectively. In the case that the number of sulfonic groups is less than 0.1 molar equivalents per 1 mole of N-phenylalkylcarbamate, the reaction hardly takes place. In the case of 1.0 to 10 molar equivalents, the reaction progresses at a suitable rate. An amount ranging from $10^1/Q$ to $10^5/Q$ of the resin is preferably employed wherein Q is a milliequivalent of sulfonic groups per one weight of the ion exchange resin (meq/g).

The aqueous inorganic acids useful for the present invention are preferably aqueous sulfuric, hydrochloric, nitric, phosphoric or boric acid, more preferably, aqueous sulfuric or phosphoric acid. The concentration of an aqueous inorganic acid may be in the range of 30 to 80% (w/w), preferably 40 to 70% (w/w). The use of less than 30% (w/w) aqueous inorganic acid prevents the production of polymethylene polyphenylalkylcarbamate wherein n in formula (III) is 2 to 5 due to a significant reduction of acidity by water. However, the reaction rate is so lowered that large amounts of by-products, N-benzyl compounds, e.g., N-(alkoxycarbonyl)phenylaminomethylphenyl and the dimer, trimer or tetramer thereof, are produced; and, thus, the yield of the desired product, 4,4-methylene-bis-(N-phenylalkylcarbamate), gets reduced. On the other hand, the use of more than 80% (w/w) aqueous inorganic acid minimizes the production of the by-products, N-benzyl compounds; however, produces a large amount of polynuclear compounds, e.g., polymethylene polyphenylalkylcarbamate, because of the high acidity of the catalyst, which reduces the yield of the desired 4,4-methylene-bis-(N-phenylalkylcarbamate).

The amount of aqueous inorganic acid used may be, therefore, crucial to the reaction rate and is generally at a weight ratio ranging from 0.1 to 5, preferably from 0.5 to 3 to one weight of N-phenylalkylcarbamate.

The molar ratio of the methylating agent to N-phenylalkylcarbamate of formula (II) is important in practising the present process because it will directly affect the selectivity of the desired compound. The molar ratio generally lies in the range from 0.01 to 1.0, preferably from 0.1 to 0.7, to separate 4,4-methylene-bis-(N-phenylalkylcarbamate) in a high selectivity. If the methylating agent is used in a ratio lower than that mentioned above, a large amount of unreacted N-phenylalkylcarbamate may remain unreacted, which obviously reduces the productivity and requires high energy for the separation, recovery and reuse of the residual N-phenylalkylcarbamate; whereas if it is used in a ratio more than the above, a large amount of polynuclear polymethylene polyphenylalkylcarbamate containing at least 3 phenyl groups is produced.

The non-polar aprotic solvent employed in the present invention is preferably to have a low solubility in water and to be separated easily from the product and the reactants after the reaction is completed, for the reason that a trace of quarternary ammonium that may be produced during the reaction and the residual acid groups which may be detrimental to the final product should be removed so as to readily obtain pure 4,4-methylene-bis-(N-phenylalkylcarbamate). In addition, only the non-polar aprotic solvent does not solvate the protons of the catalyst so as to facilitate the reaction.

The solubilities of N-phenylalkylcarbamate and the condensation products depend on the structure and polarity of the solvent employed. Preferably, the solvent may contain up to 10 carbon atoms and one or more of phenyl, halogen and ester groups and the solubility thereof in water is less than 10% (w/w). Exemplary compounds for the solvent include benzene, toluene, xylene, cyclohexane, diethylether, methylacetate, ethylacetate; preferably, benzene, toluene, xylene or cyclohexane.

It is particularly important in accordance with the present invention to use such a solvent in an amount that will dissolve 50% or less of the product of formula (III) at the reaction temperature. The undissolved product is crystallized as small crystallines in an emulsion. The yield attainable under the reaction condition is 5 to 20% greater than that obtainable when the solvent is used in an amount to dissolve 100% of the compound of formula (III).

It is preferable to employ the solvent in a weight ratio of 5 or less to one weight of N-phenylalkylcarbamate of formula (II) when a solid acid resin is used as the catalyst, and from 1 to 10, particularly from 2 to 8, when an aqueous acid is used as the catalyst.

The appropriate temperature range at which the condensation may be carried out is generally 120° C. or less, preferably from 30° to 100° C. The reaction temperature is critical to the present invention since it may directly influence the composition of isomers produced as well as the reaction rate.

The present process can be carried out under a normal pressure or a pressurized condition; and it may also be carried out under a reduced pressure, if necessary. The reaction time is generally from several minutes to several hours, depending on the reaction rate, the amount of catalyst used and the type and amount of solvent used. The reactor is preferably made of glass-or teflon to protect from the corrosion by the acid used in the reaction. In particular, teflon is preferred to avoid the formation of large solid chunks by agglomeration of the product.

The reaction can be carried out batchwise or continuously by suspending the solid resin in the reaction mixture, or utilizing the solid resin as a fixed bed, or in two-phase liquid consisting of an aqueous acid and an organic solvent dissolving N-alkylcarbamate.

One of the unexpected advantages of the present process is that the final products which are crystallized and isolated at a certain temperature in crystalline form from the reaction products in an emulsion are mainly 4,4-methylene-bis-(N-phenylalkylcarbamate). Polymethylene polyphenylalkylcarbamates having two or more nuclei are substantially dissolved in the solvent and present in the liquid phase; and, therefore, 4,4-methylene-bis-(N-phenylalkylcarbamate) can be separated by way of simple filtration. The temperature at which the separation is carried out is critical since it directly affects the purity of 4,4-methylene-bis-(N-phenylalkylcarbamate) separated. Accordingly, the separation should be carried out at a temperature greater than the melting point of N-phenylalkylcarbamate for obtaining highly pure 4,4-methylene-bis-(N-phenylalkylcarbamate). When it is carried out at a temperature lower than the melting point, a portion of unreacted N-phenylalkylcarbamate may be present as a solid form. The temperature at the separation step may vary depending on the alkyl substituents in formula (III); and generally ranges from 40° to 120° C., preferably 50° to 90° C. After the separation, the washing and drying steps are preferably carried out to remove the solvent residue and the acid groups remaining in the product, with the drying temperature being 200° C. or less, preferably within the range of 50° to 120° C. If necessary, the methylating agent may be removed by washing before and/or after the separation.

The yield of 4,4-methylene-bis-(N-phenylalkylcarbamate) which is separated as small crystalline depends on the molar ratio of the methylating agent to N-phenylalkylcarbamate of formula (II), and the structure, polarity and amount of the solvent used, etc. The separation may be carried out by employing a conventional separation method such as a filtration method under a reduced pressure and centrifugation, considering the particle size of the desired product.

This invention is further described by way of the following examples which are given for the purpose of illustration and are not to be regarded as limiting the scope of the invention. The product was analyzed by using a high performance liquid chromatography.

EXAMPLE 1

To a 1000 ml three-neck flask equipped with a condenser were added 16.0 g of an ion exchange resin having polystyrene which has a molecular weight of 50,000 as a resin-base and sulfonic groups as a functional group wherein the surface area per weight was 60 m$^2$/g, the number of sulfonic groups was 5 meq/g and the average diameter thereof was 1 mm, 15.55 g (10.30×10$^{-2}$ mole) of N-phenylmethylcarbamate, 1.67 g of 37% formalin (2.06×10$^{-2}$ mole of formaldehyde) and 34.8 g of toluene; and the resultant was reacted with stirring for 3 hours at a temperature of 90° C. An analysis of the resultant in an emulsion after the completion of reaction was carried out to determine the conversion of formaldehyde, and the selectivity for each of 4,4-methylene-bis-(N-phenylmethylcarbamate), 2,4-methylene-bis-(N-phenylmethylcarbamate), polymethylene polyphenylmethylcarbamate having three or more nuclei, and the by-products such as N-benzyl compound. The results are shown in Table 1.

The resultant in an emulsion was filtered under a reduced pressure at a temperature of 55° C. and dried at a temperature of 70° C. for 2 hours to obtain 1.78 g (5.67×10$^{-2}$ mole) of pure 4,4-methylene-bis-(N-phenylmethylcarbamate), which corresponds to 55% of total 4,4-methylene-bis-(N-phenylmethylcarbamate) produced by the condensation as shown in Table 1.

EXAMPLE 2

The same procedure as in Example 1 was repeated except that 2.78 g of 37% formalin (3.4×10$^{-2}$ mole of formaldehyde) was used. The resultant in an emulsion was analyzed as in Example 1.

The resultant was filtered and dried in the same manner as in Example 1 to obtain 2.78 g (8.85×10$^{-3}$ mole) of pure 4,4-methylene-bis-(N-phenylmethylcarbamate). The results are shown in Table 1.

EXAMPLE 3

In a fixed bed reactor for continuous flow having an inner diameter of 50 cm and a height of 10 cm which was charged with 100.0 g of the ion exchange resin used in Example 1, 59.2 g (3.92×10$^{-1}$ mole) of N-phenylmethylcarbamate, 7.94 g of 37% formalin (9.80×10$^{-2}$ mole of formaldehyde) and 132.8 g of toluene were continuously reacted for 6 hours at a temperature of 90° C. with the average residence time of 3 hours. The reaction temperature was maintained by circulating a heating medium such as silicon oil around the outside of the reactor; and the residence time of the reactants was regulated by controlling the flow rate of the reactants into the reactor. The resultant in an emulsion was analyzed as in Example 1.

The resultant was filtered and dried in the same manner as in Example 1 to obtain 8.46 g (2.70×10$^{-2}$ mole) of pure 4,4-methylene-bis-(N-phenylmethylcarbamate). The results are shown in Table 1.

EXAMPLE 4

To test the deactivation of the catalyst, 100.0 g of the ion-exchange resin was continuously reacted for 60 hours in the same reactor and under the same condition as in Example 3; and 59.2 g (3.92×10$^{-1}$ mole) of N-phenylmethylcarbamate, 7.94 g of 37% formalin (9.80×10$^{-2}$ mole of formaldehyde) and 119.1 g of cyclohexane were continuously reacted for 6 hours at a temperature of 70° C. with the average residence time of 3 hours. The resultant in an emulsion was analyzed as in Example 1.

The resultant was filtered and dried in the same manner as in Example 1 to obtain 4.30 g (1.37×10$^{-2}$ mole) of pure 4,4-methylene-bis-(N-phenylmethylcarbamate). The results are shown in Table 1.

EXAMPLE 5

To a 250 ml three-neck glass flask equipped with a condenser were added 9.70 g (6.42×10$^{-2}$ mole) of N-phenylmethylcarbamate, 2.60 g of 37% formalin (3.21×10$^{-2}$ mole of formaldehyde), 22.5 g of 50% (w/w) aqueous sulfuric acid and 55.0 g of toluene; and the reactants were reacted at a temperature of 70° C. for 3 hours with stirring. The resultant in an emulsion was analyzed as in Example 1.

The resultant was filtered under a reduced pressure at a temperature of 55° C., washed with distilled water and dried at a temperature of 90° C. for 2 hours to obtain 2.75 g (8.76×10$^{-3}$ mole) of pure 4,4-methylene-bis-(N-phenylmethylcarbamate). The results are shown in Table 1.

EXAMPLE 6

The same procedure as in Example 5 was repeated except that the amount of 37% formalin used was changed to 1.30 g (1.60×10$^{-2}$ mole of formaldehyde). The resultant in an emulsion was analyzed as in Example 1.

The resultant was filtered and dried in the same manner as in Example 5 to obtain 1.00 g (3.18×10$^{-3}$ mole) of pure 4,4-methylene-bis-(N-phenylmethylcarbamate). The results are shown in Table 1.

EXAMPLE 7

The same procedure as in Example 5 was repeated except that toluene was replaced with 55 g of cyclohexane and a reactor made of teflon was used. The resultant in an emulsion was analyzed as in Example 1.

The resultant was filtered and dried in the same manner as in Example 5 to obtain 2.65 g (8.44×10$^{-3}$ mole) of pure 4,4-methylene-bis-(N-phenylmethylcarbamate). The results are shown in Table 1.

COMPARATIVE EXAMPLE 1

The same procedure as in Example 1 was repeated except that the amount of the solvent used was changed to 85.4 g. The resultant in emulsion was analyzed as in Example 1. No 4,4-methylene-bis-(N-phenylmethylcarbamate) was crystallized and separated. The results are shown in Table 1.

COMPARATIVE EXAMPLES 2 TO 4

The same procedure as in Example 1 was repeated except that the solvent was replaced with methanol for Comparative Example 2, water for Comparative Example 3 and dimethylsulfoxide for Comparative Example 4. The resultant was analyzed as in Example 1. No 4,4-methylene-bis-(N-phenylmethylcarbamate) was crystallized and separated. The results are shown in Table 1.

COMPARATIVE EXAMPLE 5

The same procedure as in Example 5 was repeated except that toluene was not used and the amount of 50% (w/w) aqueous sulfuric acid was changed to 80.0 g. The resultant which was not in the form of an emulsion was agglomerated to form, over the wall of the reactor, a large solid chunk from which 4,4-methylene-bis-(N-phenylmethylcarbamate) was not selectively separated. The large solid chunk was dissolved with an excess amount of ethyl acetate, washed with water and neutralized with NaOH solution. The resultant was analyzed as in Example 1. The results are shown in Table 1.

COMPARATIVE EXAMPLE 6

The same procedure as in Example 5 was carried out except that 50% (w/w) aqueous sulfuric acid was replaced with 85% (w/w) aqueous sulfuric acid. The product in dark brown liquid was produced, but 4,4-methylene-bis-(N-phenylmethylcarbamate) was not selectively separated therefrom. The product was treated as in Comparative Example 5 and analyzed as in Example 1. The results are shown in Table 1.

As can be seen from the Examples and Comparative Examples, the present process has the superior and unexpected advantages of selectively separating 4,4-methylene-bis-(N-phenylmethylcarbamate), which is a precursor to pure MDI, from the condensation product; and, preparing pure MDI therefrom, without having to employ a separate step for isolating pure MDI.

While the invention has been described with respect to the above specific embodiments, it should be recognized that various modifications and changes as may be apparent to those skilled in the art to which the invention pertains may be made and also fall within the scope of the invention as defined by the claims that follow.

What is claimed is:

1. A process for preparing 4,4-methylene-bis-(N-phenylalkylcarbamate) of formula (I), which comprises:

condensing N-phenylalkylcarbamate of formula (II) with a methylating agent in the presence of an acidic ion-exchange resin or an aqueous inorganic acid as a catalyst, and a non-polar aprotic solvent to produce a condensation product; and filtrating the condensation product at a temperature greater than the melting point of N-phenylalkylcarbamate to separate 4,4-methylene-bis-(N-phenylalkylcarbamate) of formula (I):

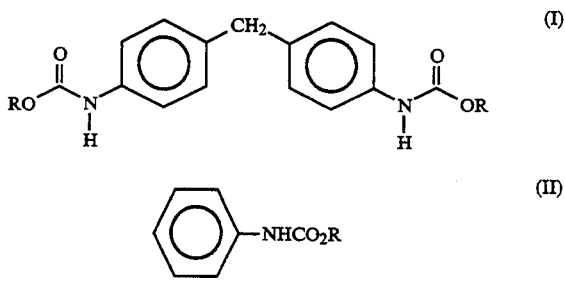

wherein:

R is a lower alkyl group having 8 or fewer carbon atoms.

2. The process of claim 1 wherein the ion-exchange resin is a styrene-based ion-exchange resin with sulfonic groups as a functional group wherein a surface area per weight is at least 50 m$^2$/g and a number of sulfonic groups per weight is at least 3 milliequivalents/g.

3. The process of claim 1 wherein the ion exchange resin is used in an amount ranging from $10 \times Q^{-1}$ to $10^5 \times Q^{-1}$ and Q represents a milliequivalent of sulfonic groups per one weight of the ion-exchange resin.

TABLE 1

| | Conversion of Formaldehyde | Selectivity (%) | | | | 4,4-MDU isolated (%) |
|---|---|---|---|---|---|---|
| | | *4,4-MDU | **PMPPU | ***2,4-MDU | N-Benzyl Compound | |
| Example No. | | | | | | |
| 1 | 71 | 72 | 10 | 18 | — | 55 |
| 2 | 68 | 69 | 16 | 15 | — | 54 |
| 3 | 70 | 70 | 15 | 15 | — | 55 |
| 4 | 30 | 68 | 3 | 9 | 20 | 69 |
| 5 | 67 | 72 | 3 | 4 | 21 | 57 |
| 6 | 75 | 81 | 2 | 4 | 13 | 46 |
| 7 | 63 | 68 | 2 | 11 | 19 | 61 |
| Comparative Example No. | | | | | | |
| 1 | 50 | 75 | 10 | 15 | — | — |
| 2 | 5 | 2 | — | — | 98 | — |
| 3 | 2 | — | — | — | 100 | — |
| 4 | 1 | — | — | — | 100 | — |
| 5 | 75 | 81 | 3 | 9 | 7 | — |
| 6 | 38 | 53 | 29 | 18 | — | — |

*4,4-FMDU: 4,4-methylene-bis-(N-phenylmethylcarbamate)
**PMPPU: polymethylene polyphenylmethylcarbamate
***2,4-MDU: 2,4-methylene-bis-(N-phenylmethylcarbamate)

4. The process of claim 1 wherein the aqueous inorganic acid is 30 to 80% (w/w) aqueous inorganic acid.

5. The process of claim 4 wherein the inorganic acid is sulfuric, phosphoric, hydrochloric, nitric or boric acid.

6. The process of claim 1 wherein the aqueous inorganic acid is used in a weight ratio ranging from 0.1 to 5 to one weight of N-phenylalkylcarbamate.

7. The process of claim 1 wherein said N-phenylalkylcarbamate has 8 or fewer carbon atoms.

8. The process of claim 1 wherein the methylating agent is dialkoxymethane, formaldehyde, paraformaldehyde, hexamethylenetetramine or trioxane or a mixture thereof.

9. The process of claim 1 wherein the molar ratio of the methylating agent to N-phenylalkylcarbamate is from 0.01 to 1.0.

10. The process of claim 1 wherein the non-polar aprotic solvent has up to 10 carbon atoms and at least one of phenyl, halogen and ester groups.

11. The process of claim 1 or 10 wherein the solubility of the non-polar aprotic solvent in water is less than 10% (w/w).

12. The process of claim 11 wherein the non-polar aprotic solvent is benzene, toluene, xylene, cyclohexane, diethylether, methyl acetate or ethyl acetate or a mixture thereof.

13. The process of claim 1 wherein the ion-exchange resin is used as a catalyst, and the non-polar aprotic solvent is used in a weight ratio of 5 or less to one weight of N-phenylalkylcarbamate.

14. The process of claim 1 wherein the aqueous inorganic acid is used as a catalyst, and the non-polar aprotic solvent is used in a weight ratio ranging from 1 to 10 to one weight of N-phenylalkylcarbamate.

15. The process of claim 1 wherein the condensation is conducted at a temperature ranging from 30° to 120° C.

16. The process of claim 1 wherein the filtration is conducted at a temperature ranging from 40° to 120° C.

* * * * *